United States Patent
Bell et al.

(10) Patent No.: US 8,680,227 B1
(45) Date of Patent: Mar. 25, 2014

(54) MANUFACTURE OF DIHYDROXY AROMATIC COMPOUNDS BY ALCOHOLYSIS OF POLYCARBONATE-CONTAINING COMPOSITIONS

(71) Applicant: Saudi Basic Industries Corporation, Riyadh (SA)

(72) Inventors: Philip Wesley Bell, Mount Vernon, IN (US); Alexander Stanislaus, Bangalore (IN); Venkata Ramanarayana Ganapathy Bhotla, Bangalore (IN); Tukaram Gunale, Bangalore (IN); Darshan Jayanna, Tumkur (IN)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 13/723,432

(22) Filed: Dec. 21, 2012

(51) Int. Cl.
*C08G 64/00* (2006.01)
*C08G 63/02* (2006.01)

(52) U.S. Cl.
USPC ........... 528/196; 528/198; 528/271; 528/272; 528/273; 528/274

(58) Field of Classification Search
USPC .................. 528/196, 198, 271, 272, 273, 274
See application file for complete search history.

(56) References Cited

U.S. PATENT DOCUMENTS

| | | | |
|---|---|---|---|
| 4,154,775 A | 5/1979 | Axelrod et al. | |
| 4,447,659 A | 5/1984 | Blewett | |
| 5,045,122 A | 9/1991 | Tindall et al. | |
| 5,266,716 A | 11/1993 | Buysch et al. | |
| 5,350,839 A | 9/1994 | Asaka et al. | |
| 5,391,802 A | 2/1995 | Buysch et al. | |
| 5,440,066 A | 8/1995 | Buysch et al. | |
| 6,787,632 B2 | 9/2004 | Phelps et al. | |
| 6,887,968 B2 | 5/2005 | Hahnsen et al. | |
| 7,094,917 B2 | 8/2006 | Ridinger et al. | |
| 7,585,930 B2 | 9/2009 | Kitahara et al. | |
| 2004/0054238 A1 | 3/2004 | Ban et al. | |
| 2004/0127720 A1 | 7/2004 | Hedrick et al. | |

FOREIGN PATENT DOCUMENTS

| EP | 1439158 A1 | 7/2004 |
|---|---|---|
| GB | 2043083 A | 10/1980 |

OTHER PUBLICATIONS

European Search Report for International Application No. 12382521.8; Date of Completion May 14, 2013; 6 pages.
JP2001302844 A English Abstract; Date of Publication Oct. 31, 2001; 2 pages.
JP2003041049 A English Abstract; Date of Publication Feb. 13, 2003; 1 page.
JP2005343840 A English Abstract; Date of Publication Dec. 15, 2005; 2 pages.
Anonymous; "Polycarbonate Recycling"; Research Disclosure; Sep. 1997; 2 pages.

*Primary Examiner* — Terressa Boykin
(74) *Attorney, Agent, or Firm* — Cantor Colburn LLP

(57) ABSTRACT

A method to produce a purified dihydroxy aromatic compound from a polycarbonate-containing composition is provided. The method includes depolymerizing the polycarbonate by alcoholysis using a titanium-based catalyst producing a dihydroxy aromatic compound and a dialkyl carbonate, recovering the dihydroxy aromatic compound as a crude dihydroxy aromatic compound; and contacting the recovered crude dihydroxyl aromatic compound with an acid in the presence of a solvent at an elevated temperature. Alternatively, the method comprises dissolving the recovered crude dihydroxyl aromatic compound in a solvent; contacting the dissolved crude dihydroxy aromatic compound with a base; and neutralizing the combination of the dissolved crude dihydroxy aromatic compound and the base with an acid.

23 Claims, No Drawings

MANUFACTURE OF DIHYDROXY AROMATIC COMPOUNDS BY ALCOHOLYSIS OF POLYCARBONATE-CONTAINING COMPOSITIONS

BACKGROUND

This disclosure is directed to methods for the manufacture of dihydroxy aromatic compounds by alcoholysis of polycarbonate-containing compositions, and in particular to methods of making bisphenol A by methanolysis of bisphenol A polycarbonate-containing compositions.

Polycarbonates are useful in the manufacture of articles and components for a wide range of applications, from automotive parts to electronic appliances. However, polycarbonates are not biodegradable and can present a significant bulk waste disposal problem. Accordingly, efforts have been made to recover valuable resources from polycarbonate wastes.

Polycarbonates can depolymerize in the presence of a catalyst to generate monomers such as bisphenol A and dimethyl carbonate. However, it is challenging to depolymerize polycarbonates in wastes, particularly, post-consumer low purity wastes, since these wastes contain various chemicals in addition to polycarbonates. These various chemicals can poison the catalyst, contaminate the products, and render the process expensive and inefficient. Thus, a cost effective process that allows the recovery of high quality products from polycarbonate wastes is continuously sought.

BRIEF DESCRIPTION

The disclosure provides a method to reduce the color of a crude dihydroxy aromatic compound, wherein the crude dihydroxy aromatic compound comprises a titanium-based transesterification catalyst. The method comprises contacting the crude dihydroxy aromatic compound with an acid in the presence of a solvent at an elevated temperature to dissolve the crude dihydroxy aromatic compound, and cooling the combination of the dissolved crude dihydroxy aromatic compound and the acid to precipitate the dihydroxy aromatic compound.

Alternatively, the method comprises dissolving the crude dihydroxy aromatic compound in a solvent; contacting the dissolved crude dihydroxy aromatic compound with a base; and neutralizing the combination of the dissolved crude dihydroxy aromatic compound and the base with an acid to precipitate the dihydroxy aromatic compound.

The disclosure also provides a method to produce a purified dihydroxy aromatic compound from a polycarbonate-containing composition. The method comprises the steps of heating the polycarbonate-containing composition in the presence of an alcohol and a titanium-based transesterification catalyst at a temperature of 70° C. to 200° C. and a pressure of 50 mbar to 40 bar producing a dihydroxy aromatic compound and a dialkyl carbonate, recovering the dihydroxy aromatic compound as a crude dihydroxy aromatic compound; contacting the recovered crude hydroxyl aromatic compound with an acid in the presence of a solvent at an elevated temperature thereby producing a purified dihydroxy aromatic compound.

Alternatively, the method comprises heating the polycarbonate-containing composition in the presence of an alcohol and a titanium-based transesterification catalyst at a temperature of 70° C. to 200° C. and a pressure of 50 mbar to 40 bar producing a dihydroxy aromatic compound and a dialkyl carbonate, recovering the dihydroxy aromatic compound as a crude dihydroxy aromatic compound; dissolving the recovered crude dihydroxy aromatic compound in a solvent; contacting the dissolved crude dihydroxy aromatic compound with a base; and neutralizing the combination of the dissolved crude dihydroxy aromatic compound and the base with an acid thereby producing a purified dihydroxy aromatic compound.

The produced dihydroxy aromatic compound can be polymerized to provide a polycarbonate composition. The disclosure is also directed to the polycarbonate composition produced.

These and other non-limiting characteristics are more particularly described below.

DETAILED DESCRIPTION

The use of a titanium-based catalyst, such as tetra(isopropyl)titanate, allows for depolymerization of polycarbonates, even in small amounts. However, the dihydroxy aromatic compounds obtained from such alcoholysis can have a yellow color. The inventors have discovered that a white dihydroxy aromatic compound such as bisphenol A can be produced by contacting the colored dihydroxy aromatic compound with an acid such as hydrochloric acid, phosphoric acid, or hypophosphorous acid, in the presence of a solvent, for example methanol or toluene at an elevated temperature. The inventors also found that the color of the crude dihydroxy aromatic compound can alternatively be reduced by treating the dissolved crude dihydroxy compound with a base such as an alkali base.

Without being bound by theory, it is believed that the dihydroxy aromatic compound formed during alcoholysis can complex with a titanium-based transesterification catalyst forming a stable colored complex. It is further believed that by employing an acid or an alkali base in the presence of a solvent, the colored complex can be hydrolyzed generating an uncomplexed dihydroxy aromatic compound thus reducing its color.

As used herein, a "polycarbonate" means compositions having repeating structural carbonate units of formula (1)

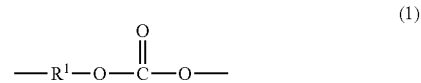

in which at least 60 percent of the total number of $R^1$ groups contain aromatic moieties and the balance thereof are aliphatic, alicyclic, or aromatic. In an embodiment, each $R^1$ is a $C_{6-30}$ aromatic group, that is, contains at least one aromatic moiety. $R^1$ can be derived from a dihydroxy compound of the formula HO—$R^1$—OH, in particular of formula (2)

$$HO\text{-}A^1\text{-}Y^1\text{-}A^2\text{-}OH \qquad (2)$$

wherein each of $A^1$ and $A^2$ is a monocyclic divalent aromatic group and $Y^1$ is a single bond or a bridging group having one or more atoms that separate $A^1$ from $A^2$. In an embodiment, one atom separates $A^1$ from $A^2$. Specifically, each $R^1$ can be derived from a dihydroxy aromatic compound of formula (3)

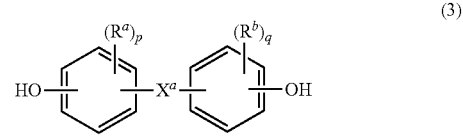

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group. In an embodiment, the bridging group $X^a$ is single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. In an embodiment, p and q is each 1, and $R^a$ and $R^b$ are each a $C_{1-3}$ alkyl group, specifically methyl, disposed meta to the hydroxy group on each arylene group.

In an embodiment, $X^a$ is a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

In another embodiment, $X^a$ is a $C_{1-18}$ alkylene group, a $C_{3-18}$ cycloalkylene group, a fused $C_{6-18}$ cycloalkylene group, or a group of the formula —B$^1$-G-B$^2$— wherein B$^1$ and B$^2$ are the same or different $C_{1-6}$ alkylene group and G is a $C_{3-12}$ cycloalkylidene group or a $C_{6-16}$ arylene group. For example, $X^a$ can be a substituted $C_{3-18}$ cycloalkylidene of formula (4)

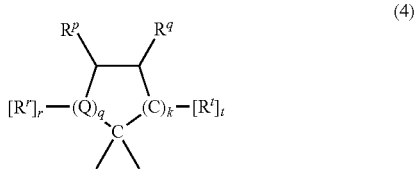

(4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is 1 and i is 0, the ring as shown in formula (4) contains 4 carbon atoms, when k is 2, the ring as shown in formula (4) contains 5 carbon atoms, and when k is 3, the ring contains 6 carbon atoms. In an embodiment, two adjacent groups (e.g., $R^q$ and $R^t$ taken together) form an aromatic group, and in another embodiment, $R^q$ and $R^t$ taken together form one aromatic group and $R^r$ and $R^p$ taken together form a second aromatic group. When $R^q$ and $R^t$ taken together form an aromatic group, $R^p$ can be a double-bonded oxygen atom, i.e., a ketone.

"Polycarbonates" includes homopolycarbonates (wherein each $R^1$ in the polymer is the same), copolymers comprising different $R^1$ moieties in the carbonate ("copolycarbonates"), copolymers comprising carbonate units and other types of polymer units, such as ester units, and combinations comprising at least one of homopolycarbonates or copolycarbonates.

Polycarbonate-containing compositions can come from various resources, e-waste being one of them. Polycarbonates, particularly flame retardant polycarbonates ("FR polycarbonates") are used in various components and housings in electronic devices. Once the devices are discarded, plastics are separated from metal and glass components and are processed to provide potential feedstocks for industrial use. These feedstocks are referred to as plastics from e-waste. Examples of polycarbonate-containing e-waste include plastics from float sink e-waste and trommel e-waste.

"Float sink e-waste" is obtained via a liquid separation process. After being ground, e-waste materials are separated according to their relative buoyancy in selected liquids in a float sink tank. For example, in such processes a first float/sink tank is filled with plain water. Polyethylene and polypropylene float, and are removed from polystyrene, acrylonitrile butadiene styrene (ABS), and FR polycarbonate, which sink. These "sinks" go into a second tank containing an aqueous solution of 1.035 g/cc density, as well as three rotating drums with paddle vanes. Polystyrene floats in this tank, while ABS and FR polycarbonate sink. The FR polycarbonate and ABS are a compatible blend, which processors sell as float sink e-waste plastics. Float sink e-waste plastics can be obtained, for example, from Global Electric and Electronic Processing (GEEP).

"Trommel e-waste" plastics are e-waste that have been ground and physically sorted via trommel screening. Trommel e-waste plastics are available, for example, from GEEP.

Other waste materials are first separated by hand prior to size reduction. Those parts believed to be primarily polycarbonate/ABS blends are then hand-picked and sampled. Such e-waste plastics are available, for example, from Recycletronics.

Optionally, the polycarbonate waste can be pre-treated with solvents to provide polycarbonate-containing compositions having a relatively high polycarbonate (PC) content. For example, polycarbonates can be isolated by extraction from recycle grade polycarbonate or e-waste plastics by pretreatment with a suitable solvent like acetone which removes flame retardants and most of the ABS. The isolated polycarbonate-containing compositions can then be used for depolymerization.

Polycarbonate-containing compositions also include FR polycarbonate resin products that contain phosphorus-containing flame retardants.

The phosphorus-containing flame retardants in the polycarbonate-containing compositions include organic phosphates and organic compounds containing phosphorus-nitrogen bonds.

One type of organic phosphate is an aromatic phosphate of the formula (GO)$_3$P=O, wherein each G is independently an alkyl, cycloalkyl, aryl, alkylaryl, or aralkyl group, provided that at least one G is an aromatic group. Two of the G groups can be joined together to provide a cyclic group, for example, diphenyl pentaerythritol diphosphite. Aromatic phosphates include, phenyl bis(dodecyl)phosphate, phenyl bis(neopentyl)phosphate, phenyl bis(3,5,5'-trimethylhexyl)phosphate, ethyl diphenyl phosphate, 2-ethylhexyl di(p-tolyl)phosphate, bis(2-ethylhexyl)p-tolyl phosphate, tritolyl phosphate, bis(2-ethylhexyl)phenyl phosphate, tri(nonylphenyl)phosphate, bis(dodecyl)p-tolyl phosphate, dibutyl phenyl phosphate, 2-chloroethyl diphenyl phosphate, p-tolyl bis(2,5,5'-trimethylhexyl)phosphate, 2-ethylhexyl diphenyl phosphate, or the like. A specific aromatic phosphate is one in which each G is aromatic, for example, triphenyl phosphate, tricresyl phosphate, isopropylated triphenyl phosphate, and the like.

Di- or polyfunctional aromatic phosphorus-containing compounds are also useful, for example, compounds of the formulae below:

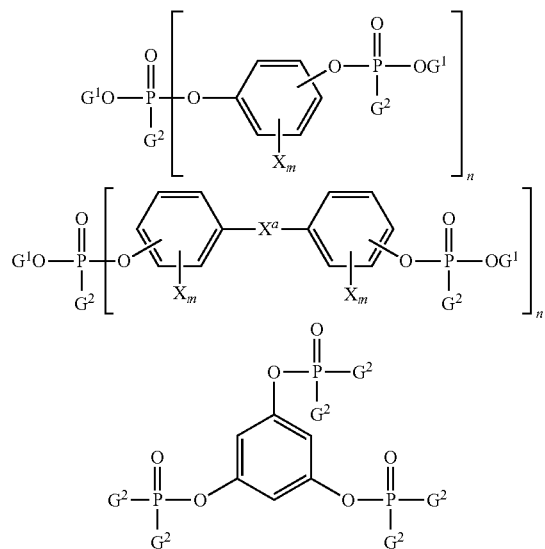

wherein each $G^1$ is independently a hydrocarbon having 1 to 30 carbon atoms; each $G^2$ is independently a hydrocarbon or hydrocarbonoxy having 1 to 30 carbon atoms; each X is independently a bromine or chlorine; m is 0 to 4, and n is 1 to 30. Di- or polyfunctional aromatic phosphorus-containing compounds include resorcinol tetraphenyl diphosphate (RDP), the bis(diphenyl)phosphate of hydroquinone and the bis(diphenyl)phosphate of bisphenol A, respectively, their oligomeric and polymeric counterparts and the like.

Exemplary suitable flame retardant compounds containing phosphorus-nitrogen bonds include phosphonitrilic chloride, phosphorus ester amides, phosphoric acid amides, phosphonic acid amides, phosphinic acid amides, and tris(aziridinyl) phosphine oxide. The organic phosphorus-containing flame retardants are generally present in amounts of about 0.1 to about 20 parts by weight, for example, about 2 to about 18 parts by weight or about 4 to about 16 parts by weight, optionally about 2 to about 15 parts by weight, based on 100 parts by weight of the total composition, exclusive of any filler.

Polycarbonates in the polycarbonate-containing compositions can be depolymerized by alcoholysis. As used herein, alcoholysis refers to a process that depolymerizes polycarbonate to produce dihydroxy aromatic compounds and dialkyl carbonates by using an alcohol as both a solvent and a reactant.

The alcohol can be a $C_{1-10}$-alcohol, for example, an alkyl alcohol such as methanol, ethanol, propanol, butanol, an aryl alcohol such as phenol, cresols, and the like. Alcoholysis in the presence of an alkyl alcohol produces a dialkyl carbonate. Alcoholysis in the presence of an aryl alcohol produces a diaryl carbonate. Where the discussion and the examples herein refer to dialkyl carbonate, it is appreciated that the alcoholysis to recover diaryl carbonate and the use of the recovered diaryl carbonate to produce polycarbonate is also within the scope of the disclosure. When methanol is used, the alcoholysis is referred to as methanolysis, when ethanol is used, the process is referred to as ethanolyis, and so forth. Where the discussion and the examples herein refer to methanolysis, the skilled artisan will understand that other alcohols can be interchangeably used for what would generally be referred to as alcoholysis and that the latter is within the scope of the invention.

Transesterification catalysts can facilitate the alcoholysis of polycarbonates. The catalyst can be one or more of titanium isopropoxide, a hydroxide of an alkali metal, a hydroxide of an alkaline earth metal, an alkali metal salt, an alkaline earth metal salt, a quaternary ammonium salt of boron hydride, a quaternary ammonium salt of aluminum hydride, a hydride of an alkali metal, a hydride of an alkaline earth metal, an aryloxide of an alkali metal, an aryloxide of an alkaline earth metal, an organic salt of an alkali metal, an organic salt of an alkaline earth metal, a boron compound, a silicon compound, a germanium compound, a tin compound, an organotin compound, a lead compound, an onium compound, an antimony compound, a manganese compound, a titanium compound, a zinc compound, or a zirconium compound.

The hydroxide of an alkali metal or an alkaline earth metal can be lithium hydroxide, sodium hydroxide, potassium hydroxide, or calcium hydroxide. The quaternary ammonium salts of boron hydride and of aluminum hydride can be lithium aluminum hydride, sodium boron hydride, and tetramethyl ammonium boron hydride. The hydrides of an alkali metal and of an alkaline earth metal can be lithium hydride, sodium hydride, or calcium hydride. The alkoxides of an alkali metal and of an alkaline earth metal can be lithium methoxide, sodium ethoxide, or calcium methoxide. The aryloxides of an alkali metal and of an alkaline earth metal may be lithium phenoxide, sodium phenoxide, magnesium phenoxide, LiO—Ar—OLi, wherein Ar represents an arylene group, and NaO—Ar—ONa, wherein Ar represents an arylene group. The organic salts of an alkali metal and of an alkaline earth metal can be lithium acetate, calcium acetate, or sodium benzoate. The zinc compounds can be zinc oxide, zinc acetate or zinc phenoxide. The boron compounds can be boron oxide, boric acid, sodium borate, trimethyl borate, tributyl borate, triphenyl borate, ammonium borate, or phosphonium borate. The silicon compounds can be silicon oxide, sodium silicate, tetraalkylsilicon, tetraarylsilicon, or diphenyl-ethyl-ethoxysilicon. The germanium compounds can be germanium oxide, germanium tetrachloride, and germanium ethoxide, or germanium phenoxide. The tin compounds can be tin oxide, dialkyltin oxide, dibutyltin oxide, dialkyltin carboxylate, or tin acetate. The tin compounds that have an alkoxy group or an aryloxy group bonded to tin can include ethyltin tributoxide and organotin compounds. Lead compounds include lead oxide, lead acetate, lead carbonate, and basic lead carbonate. Alkoxides and aryloxides of lead can also be used as a metal transesterification catalyst. One example of an aryloxide of lead is lead diphenoxide. Onium compounds can include quaternary ammonium salt, quaternary phosphonium salt, or a quaternary arsonium salt. The antimony compounds can include antimony oxide and antimony acetate. The manganese compounds can include manganese acetate, manganese carbonate and manganese borate. The titanium compounds include titanium oxide, titanium alkoxides and titanium aryloxide. The zirconium compounds include zirconium acetate, zirconium oxide, zirconium alkoxide, zirconium aryloxide, and zirconium acetylacetonate.

In addition to the foregoing, transesterification catalysts used herein can include tetrabutylammonium acetate, tetrabutylphosphonium acetate, or tetrabutylphosphonium phenolate. The transesterification catalyst as used herein can be one or more of the foregoing compounds. In specific embodiments, the catalyst is titanium tetra(isopropyl)titanate, aluminum isopropoxide, dibutyltin oxide, metal phenoxides, or a combination comprising at least one of the foregoing. Advantageously, the catalyst is a catalyst purge stream from a diphenyl carbonate production unit.

When the catalyst is a titanium-based catalyst, the catalyst can be removed by adding a sufficient amount of water to a blend of dihydroxy aromatic compound, the dialkyl compound, and the alcohol to convert the catalyst to titanium dioxide, which can be filtered off A catalytically active amount of the catalyst can be less than 4 wt %, 3 wt %, 2 wt %, 1 wt %, 0.5 wt %, 0.25 wt %, 0.1 wt %, 0.05 wt %, 0.025 wt %, 0.01 wt % based on the total weight of the polycarbonate-containing composition and the alcohol.

The alcoholysis of polycarbonate is generally conducted at a temperature of at least 30° C., specifically a temperature from 70° C. to 200° C., more specifically 100° to 180° C., most specifically 130° to 170° C. At temperatures below 30° C., reaction rates can be too slow for economical operation. Atmospheric or super-atmospheric pressures can be used, for example up to 40 bar, specifically from 50 mbar to 40 bar, more specifically from 5 bar to 20 bar autogeneous pressure.

The alcoholysis of polycarbonate can be conducted for about 0.5 to about 10 hours, specifically about 1 to about 5 hours, more specifically about 2 to about 4 hours depending on the temperature and pressure and the specific polycarbonate-containing composition and catalyst used. Advantageously, conversion of the polycarbonate is 99% complete in less than 4 hours.

A weight ratio of alcohol to polycarbonate-containing composition of 1:1 to 10:1, specifically 2:1 to 8:1, more specifically 2:1 to 6:1 can be used. A molar ratio of alcohol such as methanol, ethanol, or butanol to polycarbonate-containing composition can be 8:1 to 80:1, specifically 16:1 to 64:1, more specifically 16:1 to 48:1. While other ratios than those set out herein can be used, a slight excess of alcohol can be desirable as it is used as both a reagent and a solvent.

The combination of the alcohol and the dialkyl carbonate can be separated from the dihydroxy aromatic compound by distillation. The alcohol/dialkyl carbonate stream which contains up to 50 wt % of dialkyl carbonate can be reused for alcoholysis of polycarbonates. Alternatively, the alcohol/dialkyl carbonate mixture can be separated into an alcohol rich substream and a dialkyl carbonate rich substream with each substream containing greater than 75% of alcohol or dialkyl carbonate. The alcohol rich substream can be reused to depolymerize polycarbonates. In an embodiment, one or both of the substreams can be purified before use in further reactions.

The alcoholysis produces dihydroxy aromatic compounds and dialkyl carbonates such as dimethyl carbonate, diethyl carbonate, and dibutyl carbonate. Some illustrative examples of specific dihydroxy aromatic compounds include the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Other specific examples of dihydroxy aromatic compounds include 1,1-bis(4-hydroxyphenyl)methane, 1,1-bis(4-hydroxyphenyl)ethane, 2,2-bis(4-hydroxyphenyl)propane (also referred to as "bisphenol A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-2-methylphenyl)propane, 1,1-bis(4-hydroxy-t-butylphenyl)propane, 3,3-bis(4-hydroxyphenyl)phthalimidine, 2-phenyl-3,3-bis(4-hydroxyphenyl)phthalimidine (PPPBP), 1,1-bis(4-hydroxy-3-methylphenyl) cyclohexane (DMBPC), and 1,4:3,6-dianhydro-D-sorbitol. In one specific embodiment, the dihydroxy aromatic compound derived from the alcoholysis of polycarbonate is bisphenol A.

The use of a titanium-based catalyst, such as tetra(isopropyl)titanate, allows for depolymerization of polycarbonates, even in small amounts. However, the dihydroxy aromatic compounds obtained from such alcoholysis can have a yellow color. For example, the crude dihydroxy aromatic compound such as bisphenol A derived from alcoholysis of a polycarbonate-containing composition can have a color value on the American Public Health Association color index (referred to as "APHA values") of greater than about 2,600 when, for example, measured via a colorimeter on a 70 weight percent (weight/volume) solution in methanol versus a methanol blank, whereas a pure bisphenol A standard sample only has an APHA value of about 15 when, for example, measured using the same procedure. APHA is a single number yellowness index. A higher APHA value translates to a more yellow colored sample.

The inventors have surprisingly found that the color of the crude dihydroxy aromatic compound can be reduced by treating the crude dihydroxy compound with an acid in the presence of a solvent at an elevated temperature.

Alternatively, the color of the crude dihydroxy aromatic compound can be reduced by first optionally dissolving it in a solvent, then treating the solution with a base, followed by an acid. The dihydroxy aromatic compound precipitates out and has reduced color. The process can be conducted at room temperature. Exemplary bases include alkali bases such as sodium hydroxide and potassium hydroxide.

Exemplary acids include hydrochloric acid, phosphoric acid, phosphorous acid, hypophosphorous acid, sulphonic acid, methane sulphonic acid, toluene sulphonic acid, or a combination comprising at least one of the foregoing. In specific embodiments, the acid is hydrochloric acid, phosphorous acid, hypophosphorous acid, sulphonic acid, or a combination comprising at least one of the foregoing.

Exemplary solvents include a ketone, an alcohol, an amine, or a hydrocarbon. Combinations of the solvents can be used. Specifically, the solvent can be toluene, acetone, methylisobutylketone, methylethylketone, methanol, ethanol, isopropanol, 2-butanol, t-butanol, 1,2-ethylene glycol, dimethylamine, n-methylpyrrolidone, dimethylformamide, dimethylsulfoxide, or a combination comprising at least one of the foregoing. Advantageously, the solvent dissolves the dihydroxy aromatic compound. The elevated temperature can be the boiling temperature of the solvent.

The amount of the acid used can be 10 wt % with respect to weight of bisphenol A.

The combination of the crude dihydroxy aromatic compound, the acid, and the solvent can be heated at the elevated temperature for 10 minutes to 10 hours, specifically for 30 minutes to 5 hours depending on the specific acid and the amount of the acid used. The dihydroxy aromatic compound having less color can precipitate out once the solution is cooled.

The combination of the crude dihydroxy aromatic compound, the alkali base, and the solvent, on the other hand, does not have to be heated to an elevated temperature. Acid can be added to the combination and precipitates out the dihydroxy aromatic compound.

After the process, the color of the dihydroxy aromatic compound can be significantly reduced. For example, the APHA value can be reduced from greater than about 2,600 to less than about 800, 700, 600, 500, 400, 300, 200, 150, or 100.

When a different catalyst, for example an aluminum-based or tin-based catalyst is used in the alcoholysis of the polycarbonate-containing composition, a dihydroxy aromatic compound with less color can be obtained as compared to when a titanium-based catalyst is used in the alcoholysis.

The obtained dihydroxy aromatic compound can be sold as is or used in further reactions including polymerization to make polycarbonate. The obtained dialkyl carbonate can react with phenol to provide diphenyl carbonate. In an embodiment, the dihydroxy aromatic compound and the dialkyl carbonate can be purified before use in further reactions.

For example, the dihydroxy aromatic compound can be used to form a polycarbonate by polymerization with a carbonyl source, i.e., a carbonate precursor. Polymerization of the dihydroxy aromatic compound to produce a polycarbonate can be by interfacial or melt polymerization methods. Although the reaction conditions for interfacial polymerization can vary, a process generally involves dissolving or dispersing a dihydroxy aromatic compound in aqueous caustic soda or potash, adding the resulting mixture to a water-immiscible solvent medium, and contacting the reactants with a carbonate precursor in the presence of a catalyst such as triethylamine or a phase transfer catalyst, under controlled pH conditions, e.g., 8 to 12. The most commonly used water immiscible solvents include methylene chloride, 1,2-dichloroethane, chlorobenzene, toluene, and the like.

Carbonate precursors include a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an embodiment, an interfacial polymerization reaction to form carbonate linkages uses phosgene as a carbonate precursor, and is referred to as a phosgenation reaction.

Among the phase transfer catalysts that can be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is $Cl^-$, $Br^-$, a $C_{1-8}$ alkoxy group or a $C_{6-18}$ aryloxy group. An effective amount of a phase transfer catalyst can be 0.1 to 10 wt % based on the weight of bisphenol in the phosgenation mixture. In another embodiment an effective amount of phase transfer catalyst can be 0.5 to 2 wt % based on the weight of bisphenol in the phosgenation mixture.

Branched polycarbonate blocks can be prepared by adding a branching agent during polymerization. A chain stopper (also referred to as a capping agent) can be included during polymerization. The chain stopper limits molecular weight growth rate, and so controls molecular weight in the polycarbonate.

Alternatively, melt processes can be used to make the polycarbonates. Melt polymerization may be conducted as a batch process or as a continuous process. In either case, the melt polymerization conditions used may comprise two or more distinct reaction stages, for example, a first reaction stage in which the starting dihydroxy aromatic compound and diaryl carbonate are converted into an oligomeric polycarbonate and a second reaction stage wherein the oligomeric polycarbonate formed in the first reaction stage is converted to high molecular weight polycarbonate. Such "staged" polymerization reaction conditions are especially suitable for use in continuous polymerization systems wherein the starting monomers are oligomerized in a first reaction vessel and the oligomeric polycarbonate formed therein is continuously transferred to one or more downstream reactors in which the oligomeric polycarbonate is converted to high molecular weight polycarbonate. Typically, in the oligomerization stage the oligomeric polycarbonate produced has a number average molecular weight of about 1,000 to about 7,500 Daltons. In one or more subsequent polymerization stages, the number average molecular weight (Mn) of the polycarbonate is increased to between about 8,000 and about 25,000 Daltons (using polycarbonate standard).

The term "melt polymerization conditions" is understood to mean those conditions necessary to effect reaction between a dihydroxy aromatic compound and a diaryl carbonate in the presence of a transesterification catalyst. Typically, solvents are not used in the process, and the reactants dihydroxy aromatic compound and the diaryl carbonate are in a molten state. The reaction temperature can be about 100° C. to about 350° C., specifically about 180° C. to about 310° C. The pressure may be at atmospheric pressure, supra-atmospheric pressure, or a range of pressures from atmospheric pressure to about 15 torr in the initial stages of the reaction, and at a reduced pressure at later stages, for example about 0.2 to about 15 torr. The reaction time is generally about 0.1 hours to about 10 hours.

Catalysts used in the melt transesterification polymerization production of polycarbonates can include alpha or beta catalysts. Beta catalysts are typically volatile and degrade at elevated temperatures. Beta catalysts are therefore preferred for use at early low-temperature polymerization stages. Alpha catalysts are typically more thermally stable and less volatile than beta catalysts.

The alpha catalyst can comprise a source of alkali or alkaline earth ions. The sources of these ions include alkali metal hydroxides such as lithium hydroxide, sodium hydroxide, and potassium hydroxide, as well as alkaline earth hydroxides such as magnesium hydroxide and calcium hydroxide. Other possible sources of alkali and alkaline earth metal ions include the corresponding salts of carboxylic acids (such as sodium acetate) and derivatives of ethylene diamine tetraacetic acid (EDTA) (such as EDTA tetrasodium salt, and EDTA magnesium disodium salt). Other alpha transesterification catalysts include alkali or alkaline earth metal salts of a nonvolatile inorganic acid such as $NaH_2PO_3$, $NaH_2PO_4$, $Na_2HPO_3$, $KH_2PO_4$, $CsH_2PO_4$, $Cs_2HPO_4$, and the like, or mixed salts of phosphoric acid, such as $NaKHPO_4$, $CsNaHPO_4$, $CsKHPO_4$, and the like. Combinations comprising at least one of any of the foregoing catalysts can be used.

Possible beta catalysts can comprise a quaternary ammonium compound, a quaternary phosphonium compound, or a combination comprising at least one of the foregoing. The quaternary ammonium compound can be a compound of the structure $(R^4)_4N^+X^-$, wherein each $R^4$ is the same or different, and is a $C_{1-20}$ alkyl group, a $C_{4-20}$ cycloalkyl group, or a $C_{4-20}$ aryl group; and $X^-$ is an organic or inorganic anion, for example a hydroxide, halide, carboxylate, sulfonate, sulfate, formate, carbonate, or bicarbonate. Examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often used. The quaternary phosphonium compound can be a compound of the structure $(R^5)_4P^+X^-$, wherein each $R^5$ is the same or different, and is a $C_{1-20}$ alkyl group, a $C_{4-20}$ cycloalkyl group, or a $C_{4-20}$ aryl group; and $X^-$ is an organic or inorganic anion, for example a hydroxide, halide, carboxylate, sulfonate, sulfate, formate, carbonate, or bicarbonate. Where $X^-$ is a polyvalent anion such as carbonate or sulfate it is understood that the positive and negative charges in the quaternary ammonium and phosphonium structures are properly balanced. For example, where $R^{20}$-$R^{23}$ are each methyl groups and $X^-$ is carbonate, it is understood that $X^-$ represents $2(CO_3^{-2})$. Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate, tetraphenyl phosphonium phenoxide, and combinations comprising at least one of the foregoing. TBPA is often used.

The amount of alpha and beta catalyst used can be based upon the total number of moles of dihydroxy compound used in the polymerization reaction. When referring to the ratio of beta catalyst, for example, a phosphonium salt, to all dihydroxy compounds used in the polymerization reaction, it is convenient to refer to moles of phosphonium salt per mole of the dihydroxy compound, meaning the number of moles of phosphonium salt divided by the sum of the moles of each individual dihydroxy compound present in the reaction mixture. The alpha catalyst can be used in an amount sufficient to provide $1\times10^{-2}$ to $1\times10^{-8}$ moles, specifically, $1\times10^{-4}$ to $1\times10^{-7}$ moles of metal per mole of the dihydroxy compounds used. The amount of beta catalyst (e.g., organic ammonium or phosphonium salts) can be $1\times10^{-2}$ to $1\times10^{-5}$, specifically $1\times10^{-3}$ to $1\times10^{-4}$ moles per total mole of the dihydroxy compounds in the reaction mixture.

Branched polycarbonate blocks can be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl)alpha, alpha-dimethyl benzyl)phenol), 4-chloroformyl phthalic anhydride, trimesic acid, and benzophenone tetracarboxylic acid. The branching agents can be added at a level of 0.05 to 2.0 weight %. Mixtures comprising linear polycarbonates and branched polycarbonates can be used.

The content of the following branching structures is 2,000 ppm or below.

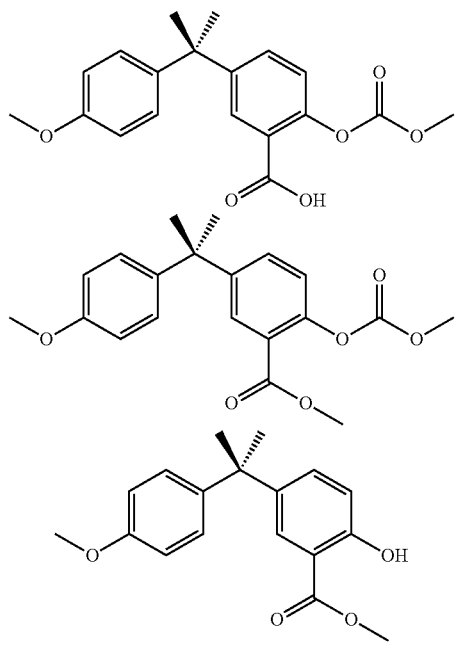

In certain embodiments, a method to reduce the color of a crude dihydroxy aromatic compound, wherein the crude dihydroxy aromatic compound comprises a titanium-based transesterification catalyst, and wherein the crude dihydroxy aromatic compound has an APHA value above about 2,000 (for example, as measured via a colorimeter on a 70 weight percent (weight/volume) solution in methanol versus a methanol blank), the method comprises contacting the crude dihydroxy aromatic compound with an acid in the presence of a solvent at an elevated temperature to dissolve the crude dihydroxy aromatic compound, and cooling the combination of the dissolved crude dihydroxy aromatic compound and the acid to precipitate the dihydroxy aromatic compound, wherein the precipitated dihydroxy aromatic compound has an APHA value below about 800 (measured, for example, via a colorimeter on a 70 weight percent (weight/volume) solution in methanol versus a methanol blank). In another embodiment, a method to reduce the color of a crude dihydroxy aromatic compound, wherein the crude dihydroxy aromatic compound comprises a titanium-based transesterification catalyst, wherein the crude dihydroxy aromatic compound has an APHA value above about 2,000 (for example as measured via a colorimeter on a 70 weight percent (weight/volume) solution in methanol versus a methanol blank) wherein the method comprises dissolving the crude dihydroxy aromatic compound with a solvent; contacting the dissolved crude dihydroxy aromatic compound with a base; and neutralizing the combination of the dissolved crude dihydroxy aromatic compound and the base with an acid to precipitate the dihydroxy aromatic compound, wherein the precipitated dihydroxy aromatic compound has an APHA value below about 800 (measured, for example, via a colorimeter on a 70 weight percent (weight/volume) solution in methanol versus a methanol blank). In either of these embodiments, optionally: the dihydroxy aromatic compound is bisphenol A; the catalyst is tetra(isopropyl)titanate; the acid is hydrochloric acid, phosphoric acid, sulphonic acid, hypophosphorous acid, or a combination comprising at least one of the foregoing; the solvent is a ketone, an alcohol, an amine, a hydrocarbon, or a combination comprising at least one of the foregoing, for example, the solvent is toluene, acetone, methylisobutylketone, methylethylketone, methanol, ethanol, isopropanol, 2-butanol, t-butanol, 1,2-ethylene glycol, dimethylamine, n-methylpyrrolidone, dimethylformamide, dimethylsulfoxide, or a combination comprising at least one of the foregoing; the base is sodium hydroxide, potassium hydroxide, or a combination thereof.

Alternatively, a method to produce a dihydroxy aromatic compound having an APHA value of lower than about 800 (measured, for example, via a colorimeter on a 70 weight percent (weight/volume) solution in methanol versus a methanol blank) from a polycarbonate-containing composition, comprises heating the polycarbonate-containing composition in the presence of an alcohol and a titanium-based transesterification catalyst at a temperature of 70° C. to 200° C. and a pressure of 50 mbar to 40 bar producing a dihydroxy aromatic compound and a dialkyl carbonate, recovering the dihydroxy aromatic compound as a crude dihydroxy aromatic compound having an APHA value of greater than about 2000 (for example, as measured via a colorimeter on a 70 weight percent (weight/volume) solution in methanol versus a methanol blank); contacting the recovered crude hydroxyl aromatic compound with an acid in the presence of a solvent at an elevated temperature thereby producing a purified dihydroxy aromatic compound having an APHA value of lower than about 800 (measured, for example, via a colorimeter on a 70 weight percent (weight/volume) solution in methanol versus a methanol blank); or a method to produce a dihydroxy aromatic compound having an APHA value of lower than about 800 (measured, for example, via a colorimeter on a 70 weight percent (weight/volume) solution in methanol versus a methanol blank) from a polycarbonate-containing composition, comprises heating the polycarbonate-containing composition in the presence of an alcohol and of a titanium-based transesterification catalyst at a temperature of 70° C. to 200° C. and a pressure of 50 mbar to 40 bar producing a dihydroxy aromatic compound and a dialkyl carbonate, recovering the dihydroxy aromatic compound as a crude dihydroxy aromatic compound having an APHA value of greater than about 2000 (measured, for example, via a colorimeter on a 70 weight percent (weight/volume) solution in methanol versus a methanol blank); dissolving the recovered crude dihydroxy aromatic compound in a solvent; contacting the dissolved crude dihydroxy aromatic compound with a base; and neutralizing the combination of the dissolved crude dihydroxy aromatic compound and the base with an acid thereby producing a purified dihydroxy aromatic compound having an APHA value of lower than about 800. In any of these embodiment, optionally: the dihydroxy aromatic compound is bisphenol A; the catalyst is tetra(isopropyl)titanate; the acid is hydrochloric acid, phosphoric acid, sulphonic acid, hypophosphorous acid, or a combination comprising at least one of the foregoing; the solvent is a ketone, an alcohol, an amine, a hydrocarbon, or a combination comprising at least one of the foregoing, for example the solvent is toluene, acetone, methylisobutylketone, methylethylketone, methanol, ethanol, isopropanol, 2-butanol, t-butanol, 1,2-ethylene glycol, dimethylamine, n-methylpyrrolidone, dimethylformamide, dimethylsulfoxide, or a combination comprising at least one of the foregoing; the base is sodium hydroxide, potassium hydroxide, or a combination thereof; the polycarbonate-containing composition comprises a phosphorus-containing flame retardant; the polycarbonate-containing composition comprises acrylonitrile butadiene styrene; or the alcohol is methanol.

In another embodiment, a method to manufacture a polycarbonate composition comprises heating a polycarbonate-containing composition in the presence of an alcohol and a titanium-based transesterification catalyst at a temperature of 70° C. to 200° C. and a pressure of 50 mbar to 40 bar producing a dihydroxy aromatic compound and a dialkyl carbonate, recovering the dihydroxy aromatic compound as a crude dihydroxy aromatic compound having an APHA value of greater than about 2000 (measured, for example, via a colorimeter on a 70 weight percent (weight/volume) solution in methanol versus a methanol blank); contacting the recovered crude hydroxyl aromatic compound with an acid in the presence of a solvent at an elevated temperature to provide a purified dihydroxy aromatic compound having an APHA value of lower than about 800; and polymerizing the purified dihydroxy aromatic compound and a carbonyl source to provide the polycarbonate composition. Alternatively, a method to manufacture a polycarbonate composition comprises heating a polycarbonate-containing composition in the presence of an alcohol and a titanium-based transesterification catalyst at a temperature of 70° C. to 200° C. and a pressure of 50 mbar to 40 bar producing a dihydroxy aromatic compound and a dialkyl carbonate, recovering the dihydroxy aromatic compound as a crude dihydroxy aromatic compound having an APHA value of greater than about 2000 (measured, for example, via a colorimeter on a 70 weight percent (weight/volume) solution in methanol versus a methanol blank); dissolving the recovered crude hydroxyl aromatic compound in a solvent; contacting the dissolved crude dihydroxy aromatic compound with a base; neutralizing the combination of the dissolved crude dihydroxy aromatic compound and the base with an acid to provide a purified dihydroxy aromatic compound having an APHA value of lower than about 800; and polymerizing the purified dihydroxy aromatic compound to provide the polycarbonate composition.

The various embodiments are further illustrated by the following non-limiting examples.

EXAMPLES

The materials used in the Examples or produced by the processes of the Examples are described in Table 1.

TABLE 1

| Component | Description | Source |
|---|---|---|
| Polycarbonate Feedstock #1 | A polycarbonate feedstock containing about 70 wt % of bisphenol A polycarbonate; about 17 wt % of acrylonitrile-butadiene-styrene resin; and about 11 wt % of bisphenol A bis(diphenyl phosphate). | SABIC |
| Polycarbonate Feedstock #2 (Red) | A polycarbonate feedstock containing about 70 wt % of bisphenol A polycarbonate; about 17 wt % of acrylonitrile-butadiene-styrene resin; and about 11 wt % of bisphenol A bis(diphenyl phosphate) with a red color package | SABIC |
| PC | Bisphenol A Polycarbonate resin, interfacial polymerization, Mw about 30,000 g/mol as determined by GPC using polycarbonate standards | SABIC |
| BPA standard | 4,4'-(propane-2,2-diyl)diphenol | SABIC |
| Al-isopropoxide | Aluminum isopropoxide | Sigma Aldrich |
| Dibutyltin oxide | | Sigma Aldrich |
| Zn acetate | Zinc acetate | Sigma Aldrich |
| Ti-isopropoxide (TPT) | Titanium (IV) isopropoxide | Sigma Aldrich |
| TMAH | Tetramethylammonium hydroxide | Sigma Aldrich |
| Tyzar* IAM | Titanate-Phosphate Complex containing 69-71 wt % of titanium chelate, 19-25 wt % of isopropyl alcohol, and 4-10 wt % of ethyl alcohol | DuPont |
| Phosphoric acid | 85% pure orthophosphoric acid | Sigma Aldrich |
| Hypophosphorous acid | 60% Hypophosphorous acid | Sigma Aldrich |
| Sulfonic acid | | |
| Methane sulfonic acid | | Sigma Aldrich |
| p-Toluene sulfonic acid | | Sigma Aldrich |
| Methanol | | Merck |
| BPA | 4,4'-(propane-2,2-diyl)diphenol | Alcoholysis product |
| DMC | Dimethyl carbonate | Alcoholysis product |

Testing Methods.

The American Public Health Association color index (APHA) of the samples was measured on a 70 weight percent (weight/volume) solution in methanol using a Macbeth color eye 7000A instrument. The APHA shift relative to the blank (methanol) is given as the APHA of the sample.

Example 1

43 g of standard BPA was dissolved in 300 ml of methanol to form a clear solution. After 0.2 g of Ti-isopropoxide catalyst was added the solution turned yellow. The solution had an APHA value of 2112 (sample A). A 100 ml sample of this yellow solution was taken, and 50 ml of 15% NaOH solution was added at room temperature. There was a reduction in the yellow color of the solution. The solution was neutralized with 50% HCl solution until the precipitation of BPA was complete. The APHA of the obtained BPA was measured to be 612.

Example 2

43 g of standard BPA was dissolved in 300 ml of methanol to form a clear solution. Then 0.2 g of Ti-isopropoxide catalyst was added to the solution. The solution turned yellow. A 100 ml sample of this yellow solution was taken, and 50 ml of 5% HCl solution was added and heated for 30 min at 100° C. The solution turned colorless, and the mixture was brought to room temperature. Water was added until precipitation was complete. The precipitated BPA was filtered. The APHA value of the obtained BPA was measured to be 56. Prior to acid treatment, the BPA sample (sample A) had an APHA of 2112.

Examples 3-14

A series of experiments were carried out to reduce the color of crude BPA obtained from methanolysis of polycarbonate-containing compositions. The color values of the samples on the American Public Health Association color index (referred to as "APHA values") are listed in Table 2. These experiments showed that BPA purity could be improved by toluene crystallization in the presence of an acid. Recrystallization of crude BPA with toluene enhances the purity from 79% to 99.7%. The results of various acids on the color by toluene crystallization have been tabulated along with the APHA value on Table 2.

Example 3

This example illustrates the methanolysis of polycarbonate feedstock #1 with Ti-isopropoxide catalyst.

Methanolysis studies were conducted in a 2 liter (titanium) Amar High Pressure Reactor equipped with a heating jacket with a jacket oil heater and a cooling coil with a cooling water tank. The reactor was also equipped with a bottom discharge valve to take out the reaction mass. Prior to commencement of each experiment, the reactor was flushed several times with pressurized nitrogen, thereby ensuring an oxygen free atmosphere inside the reactor. Then the reactor was charged with 100 g of polycarbonate feedstock #1, 600 g of methanol and 266 mg (0.04 wt %) of TPT. The reactor was again flushed several times with pressurized nitrogen. This also ensured zero leak conditions of the system. The speed of agitation was then adjusted to the desired value. The reactor contents were heated to 150° C. by circulating hot oil through the reactor jacket with an autogeneous pressure of 13 bar. The temperature of the reactor was controlled within ±0.5° C. of the set temperature by circulating cold water through the cooling coil. Once the desired temperature was reached, the time was noted as time zero. The entire system was thus operated in a batch mode for 180 min. At the end of the experiment, the reactor contents were cooled to 25°-30° C. by circulating cooling water through the cooling coil. The reactor was then depressurized to atmospheric pressure manually by opening the vent valve, and the reactor contents were drained by using the bottom drain valve.

After removal of the reaction mass, acetone (1 L) was added to the reactor and was heated to 90°-100° C. for 2-3 hr. During washing the styrene-acrylonitrile part of the ABS formed a suspension in the acetone, which collapsed the ABS into the acetone as a fine filterable suspension. The suspension was then distilled to recover acetone.

The reaction mixture containing BPA, methanol, and DMC was filtered and the insoluble separated. The filtrate was distilled to remove methanol and DMC. The APHA value of the solid BPA left behind was measured to be 2662.

The crude BPA was recrystallized in toluene without using any acid. The APHA value of the obtained BPA (sample B) increased and was measured to be 2882.

Example 4

25 g of the crude BPA from Example 3 was treated with 125 ml toluene and 10 ml of 5% HCl and heated to 110° C. for 1 hr without significant reduction in color. An additional 40 ml 5% HCl was added and heated for 2 more hrs. Reduction in color was observed and the mixture was cooled to room temperature. Solid material that separated on cooling was filtered and washed with toluene followed by water. Results for Example 4 are shown in Table 2.

Example 5

Example 4 was repeated except that 5% HCl was replaced with 5% phosphoric acid. The process and conditions were otherwise identical to those described in Example 4. Results for Example 5 are shown in Table 2.

Example 6

Example 4 was repeated except that 5% HCl was replaced with 5% hypophosphorous acid. The process and conditions were otherwise identical to those described in Example 4. Results for Example 6 are shown in Table 2.

Example 7

Example 3 was repeated except that the polycarbonate used was red colored (polycarbonate feedstock #2) instead of the grey colored polycarbonate used in Example 3 (polycarbonate feedstock #1). The process and conditions were otherwise identical to those described in Example 3. Results for Example 7 are shown in Table 2.

Example 8

Example 4 was repeated except that the sample from Example 3 was replaced by sample from Example 7. Also 5% HCl was replaced with 1% methane sulphonic acid with respect to bisphenol A. The process and conditions were otherwise identical to those described in Example 4. Results for Example 8 are shown in Table 2.

Example 9

Example 8 was repeated except that 1% methane sulphonic acid was replaced with 1% toluene sulphonic acid with respect to bisphenol A. The process and conditions were otherwise identical to those described in Example 7. Results for Example 9 are shown in Table 2.

TABLE 2

| SAMPLE | | APHA |
|---|---|---|
| Control | BPA Standard | 15 |
| A | Standard BPA + TPT catalyst | 2112 |
| Example 1 | Standard BPA + TPT catalyst + NaOH + HCl | 612 |
| Example 2 | Standard BPA + TPT catalyst treated with aq. HCl | 56 |
| Example 3 | Crude BPA from methanolysis of polycarbonate feedstock 1 with Ti-isopropoxide catalyst | 2662 |
| B | Crude BPA from Example 3 on toluene crystallization without using any acid | 2882 |
| Example 4 | Crude BPA from Example 3 was toluene crystallized in presence of 5% HCl | 710 |
| Example 5 | Crude BPA from Example 3 was toluene crystallized in presence of 5% Phosphoric acid | 125 |
| Example 6 | Crude BPA from Example 3 was toluene crystallized in presence of 5% hypophosphorous acid | 285 |
| Example 7 | Crude BPA from methanolysis of polycarbonate feedstock #2 with Ti-isopropoxide catalyst | 3300 |
| Example 8 | Crude BPA from Example 6 on toluene crystallization with methane sulphonic acid | 1880 |
| Example 9 | Crude BPA from Example 6 on toluene crystallization with toluene sulphonic acid | 2058 |

Examples 10-12

Methanolysis was also demonstrated on polycarbonate feedstock #1 with dibutyltin oxide, aluminum isopropoxide, and tetra(isopropyl)titanate plus phosphoric acid. The results are shown in Table 3. In these experiments, the color of BPA was reduced as compared to when Ti-isopropoxide was used. Yield and purity of BPA obtained was similar in all cases.

Example 10

Example 3 was repeated except that the catalyst employed in place of Ti-isopropoxide was 266 mg (0.04 wt %) of Ti-isopropoxide catalyst along with 65 mg of phosphoric acid (Ti-isopropoxide:phosphoric acid 1:0.6). The process and conditions were otherwise identical to those described in Example 3. Results for Example 10 are shown in Table 3.

Example 11

Example 3 was repeated except that the catalyst employed in place of Ti-isopropoxide was Al-isopropoxide. The process and conditions were otherwise identical to those described in Example 3. Results for Example 11 are shown in Table 3.

Example 12

Example 3 was repeated except that the catalyst employed in place of Ti-isopropoxide was dibutyltin oxide. The process and conditions were otherwise identical to those described in Example 3. Results for Example 12 are shown in Table 3.

Example 13

Example 3 was repeated except that the catalyst employed in place of Ti-isopropoxide was Tyzar IAM and polycarbonate feedstock 1 was replaced by PC. The process and conditions were otherwise identical to those described in Example 3. Results for Example 13 are shown in Table 3.

Example 14

Example 3 was repeated except that the catalyst employed in place of Ti-isopropoxide was zinc acetate. The process and conditions were otherwise identical to those described in Example 3. Results for Example 14 are shown in Table 3. Zinc acetate as catalyst did not work well as the yield was very low. The APHA for this sample was not measured.

TABLE 3

| Ex. No. | Reactant (wt % of PC) | Catalyst | BPA yield (wt %) | BPA purity | APHA |
|---|---|---|---|---|---|
| 10 | Polycarbonate feedstock #1 (70) | Ti-isopropoxide/ Phosphoric acid | 83 | (wt %) | 2170 |
| 11 | Polycarbonate feedstock #1 (70) | Al isopropoxide | 82 | 77.5 | 1212 |
| 12 | Polycarbonate feedstock #1 (70) | Dibutyl tin oxide | 87 | 79.9 | 1700 |
| 13 | PC (100)100 | Tyzar IAM | 97 | 96.3 | 2391 |
| 14 | Polycarbonate feedstock (70) | Zinc Acetate | 14 | 29 | Not measured |

The singular forms "a," "an," and "the" include plural referents unless the context clearly dictates otherwise. "Or" means "and/or." Thus, reference to "compositions containing flame retardant or ABS," for example, means compositions containing flame retardant, ABS, or both. The endpoints of all ranges directed to the same component or property are inclusive and independently combinable. Unless defined otherwise, technical and scientific terms used herein have the same meaning as is commonly understood by one of skill in the art to which this invention belongs.

As used herein, a "combination" is inclusive of blends, mixtures, alloys, reaction products, and the like. Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

As used herein, the term "hydrocarbyl" and "hydrocarbon" refers broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicyclic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxy groups; $C_{6-19}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi ($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ alkylenearyl having 1 to 3 separate or fused rings and from 6 to 18 ring carbon atoms, with benzyl being an exemplary arylalkyl group; or arylalkoxy having 1 to 3 separate or fused rings and from 6 to 18 ring carbon atoms, with benzyloxy being an exemplary arylalkoxy group.

All references cited herein are incorporated by reference in their entirety. While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method to reduce the color of a crude dihydroxy aromatic compound, wherein the crude dihydroxy aromatic compound comprises a titanium-based transesterification catalyst,
the method comprising
contacting the crude dihydroxy aromatic compound with an acid in the presence of a solvent at an elevated temperature to dissolve the crude dihydroxy aromatic compound, and
cooling the combination of the dissolved crude dihydroxy aromatic compound and the acid to precipitate the dihydroxy aromatic compound.

2. The method of claim 1, wherein the dihydroxy aromatic compound is bisphenol A.

3. The method of claim 1, wherein the catalyst is tetra(isopropyl)titanate.

4. The method of claim 1, wherein the acid is hydrochloric acid, phosphoric acid, sulphonic acid, hypophosphorous acid, or a combination comprising at least one of the foregoing.

5. The method of claim 1, wherein the solvent is a ketone, an alcohol, an amine, a hydrocarbon, or a combination comprising at least one of the foregoing.

6. The method of claim 1, wherein the solvent is toluene, acetone, methylisobutylketone, methylethylketone, methanol, ethanol, isopropanol, 2-butanol, t-butanol, 1,2-ethylene glycol, dimethylamine, n-methylpyrrolidone, dimethylformamide, dimethylsulfoxide, or a combination comprising at least one of the foregoing.

7. A method to reduce the color of a crude dihydroxy aromatic compound, wherein the crude dihydroxy aromatic compound comprises a titanium-based transesterification catalyst,
the method comprising
dissolving the crude dihydroxy aromatic compound in a solvent;

contacting the dissolved crude dihydroxy aromatic compound with a base; and neutralizing the combination of the dissolved crude dihydroxy aromatic compound and the base with an acid to precipitate the dihydroxy aromatic compound.

8. The method of claim 7, wherein the base is sodium hydroxide, potassium hydroxide, or a combination thereof.

9. A method to produce a purified dihydroxy aromatic compound from a polycarbonate-containing composition, comprising heating the polycarbonate-containing composition in the presence of an alcohol and a titanium-based transesterification catalyst at a temperature of 70° C. to 200° C. and a pressure of 50 mbar to 40 bar producing a dihydroxy aromatic compound and a dialkyl carbonate, recovering the dihydroxy aromatic compound as a crude dihydroxy aromatic compound;

contacting the recovered crude hydroxyl aromatic compound with an acid in the presence of a solvent at an elevated temperature thereby producing a purified dihydroxy aromatic compound.

10. The method of claim 9, wherein the dihydroxy aromatic compound is bisphenol A.

11. The method of claim 9, wherein the catalyst is tetra(isopropyl)titanate.

12. The method of claim 9, wherein the acid is hydrochloric acid, phosphoric acid, sulphonic acid, hypophosphorous acid, or a combination comprising at least one of the foregoing.

13. The method of claim 9, wherein the solvent is a ketone, an alcohol, an amine, a hydrocarbon, or a combination comprising at least one of the foregoing.

14. The method of claim 9, wherein the solvent is toluene, acetone, methylisobutylketone, methylethylketone, methanol, ethanol, isopropanol, 2-butanol, t-butanol, 1,2-ethylene glycol, dimethylamine, n-methylpyrrolidone, dimethylformamide, dimethylsulfoxide, or a combination comprising at least one of the foregoing.

15. A method to produce a purified dihydroxy aromatic compound from a polycarbonate-containing composition, comprising heating the polycarbonate-containing composition in the presence of an alcohol and of a titanium-based transesterification catalyst at a temperature of 70° C. to 200° C. and a pressure of 50 mbar to 40 bar producing a dihydroxy aromatic compound and a dialkyl carbonate, recovering the dihydroxy aromatic compound as a crude dihydroxy aromatic compound;

dissolving the recovered crude dihydroxy aromatic compound in a solvent;

contacting the dissolved crude dihydroxy aromatic compound with a base; and neutralizing the combination of the dissolved crude dihydroxy aromatic compound and the base with an acid thereby producing a purified dihydroxy aromatic compound.

16. The method of claim 15, wherein the base is sodium hydroxide, potassium hydroxide, or a combination thereof.

17. The method of claim 15, wherein the polycarbonate-containing composition comprises a phosphorus-containing flame retardant.

18. The method of claim 15, wherein the polycarbonate-containing composition comprises acrylonitrile butadiene styrene.

19. The method of claim 15, wherein the alcohol is methanol.

20. A method for the manufacture of a polycarbonate comprising polymerizing the purified dihydroxy aromatic compound of claim 9 and a carbonyl source to provide the polycarbonate.

21. A method for the manufacture of a polycarbonate composition comprising polymerizing the purified dihydroxy aromatic compound of claim 15 and a carbonyl source to provide the polycarbonate composition.

22. A polycarbonate composition manufactured by the method of claim 20.

23. A polycarbonate composition manufactured by the method of claim 21.

* * * * *